United States Patent [19]
Kasman

[11] Patent Number: 5,874,667
[45] Date of Patent: Feb. 23, 1999

[54] BLOCK-TYPE HEATER ASSEMBLY FOR ISOTHERMALLY HEATING SAMPLES WITH OBSERVATION ACCESS

[76] Inventor: David H. Kasman, 19 Ridge Rd., Holliston, Mass. 01746

[21] Appl. No.: 884,016

[22] Filed: Jun. 27, 1997

[51] Int. Cl.⁶ .................................................. G01N 25/00
[52] U.S. Cl. ......................... 73/61.46; 73/61.41; 374/16; 374/25
[58] Field of Search .............................. 73/61.41, 61.43, 73/61.46; 374/16, 25

[56] References Cited

U.S. PATENT DOCUMENTS

| | | | |
|---|---|---|---|
| 3,926,038 | 12/1975 | Wunning et al. | 73/61.43 |
| 4,484,822 | 11/1984 | Hancock | 374/16 |
| 4,927,270 | 5/1990 | Bonnard | 374/16 |
| 4,960,992 | 10/1990 | Vetal et al. | 73/863.12 |
| 5,092,679 | 3/1992 | Brotz | 374/16 |

OTHER PUBLICATIONS

MEL–TEMP Capillary Melting Point Apparatus, Laboratory Devices Inc. with Instructions, MEL_TEMP II Instruction.

*Primary Examiner*—Max H. Noori
*Attorney, Agent, or Firm*—Cesari and McKenna, LLP

[57] ABSTRACT

A block-type heater assembly for use in melting point/boiling point determination apparatus or other applications in which it is desirable to provide a substantially isothermal region for samples under test as well as a temperature sensor while also providing access for observation, visual or otherwise, of the samples.

15 Claims, 2 Drawing Sheets

BLOCK-TYPE HEATER ASSEMBLY FOR ISOTHERMALLY HEATING SAMPLES WITH OBSERVATION ACCESS

CROSS-REFERENCES TO RELATED APPLICATIONS AND PATENTS

The following commonly owned application is related to the present invention and is hereby incorporated by reference:

U.S. Ser. No, 08/550,632, filed on Oct. 31, 1995, entitled "Apparatus For Semi-Automatically Or Automatically Determining The Melting Point Or Other Temperature-Related Characteristics Of A Substance," naming the present applicant, David H. Kasman, as inventor.

BACKGROUND OF THE INVENTION

1. Field of the Invention

The present invention relates generally to the field of heaters for use in analytical or test instruments and, more specifically, to a block-type heater assembly which provides very uniform heating and improved temperature measurement accuracy while allowing observation of samples contained within capillary tubes inserted into the heater assembly.

2. Discussion of the Related Art

In many types of analytical testing, including melting point or boiling point determinations, it is necessary to heat one or more samples (which arm usually placed in containers) in a controlled fashion while allowing observation of the samples in order to record events of interest. Designing a suitable heater for such testing requires the solution of several problems including, among others, providing access for observation of the samples, providing for substantially uniform heating of the samples, providing a way to accurately monitor the temperature of the samples, and providing a mechanism which is inexpensive to manufacture and will reliably operate when subjected to a large number of repetitive tests over many years.

In general, two families or types of heaters llave been developed to address the foregoing problems: the oil bath-type heater and the block-type heater. Oil bath-type heaters are generally recognized as providing superior performance in terms of heating uniformity and temperature measurement accuracy. Containers in which samples are held are immersed in a stirred volume of oil. A thermometer or temperature sensor is used to measure the temperature of the oil, which is fairly constant throughout the bath. However, there are several disadvantages which are inherent to such heaters including ability to practically provide for viewing of sample containers once immersed in the oil, temperature the inconvenience and housekeeping related to handling oil, and the relatively high cost of such heaters.

Conventional block-type heaters consist essentially of a block of material, usually a metal such as aluminum, having an embedded or attached heating element The block includes apertures or recesses into which sample-bearing containers may be placed. A thermometer or temperature sensor is usually inserted into or placed in contact with the block to measure temperature While less costly and more convenient to use than oil bath heaters, block-type heaters are generally recognized as providing less uniform heating and reduced measurement accuracy. Both of those disadvantages are typically caused, at least in part, by the geometry of the block, the placement of the sample containers and the temperature sensor relative to each other or the heating element, the necessity of providing access for observation of the samples or a combination of same. Some conventional block-type heaters attempt to compensate for such deficiencies through the use of insulation. That approach is usually unsatisfactory because of limitations in the types of insulation material suitable for use with heaters operating at relatively high temperatures and difficulty in physically placing insulation where needed. In addition, the introduction of insulation creates the potential for trapping contaminants and renders the heater more difficult to clean.

SUMMARY OF THE INVENTION

In brief summary, the present invention provides a block-type heater assembly which may be used in devices or applications in which it is desirable to uniformly heat one or more samples while allowing access to observe the samples. Such applications particularly include determining the melting point or boiling point of a substance by way of visual observation.

In a preferred embodiment, a substantially rectangular block of aluminum is formed such that a plurality of slots or passages for receiving capillary tubes are defined in one of tie broad surfaces or faces of the block. The slots extend from one edge (the top) of the block to approximately the middle of the block. The slots are shaped such that a large portion of the circumference and length of each capillary tube is touching or in close proximity to the walls of the slots, thereby promoting the transfer of thermal energy to the capillary tubes. Further, because the slots are open to the surface of the block the capillary tubes and samples contained therein may be observed by way of an optical assembly which is attached to that surface, the assembly providing a light diffuser for directing a light source on the samples and a magnifying lens for viewing.

The block is preferably heated by two electric heating elements which, as compared with a single element, permits use of lower watt density, provides extended operating life of the beating elements and reduces instances of "hot spots." The heating elements are respectively disposed within apertures which are oriented substantially parallel to the slots and extend through essentially the full length of the block. The heating element apertures are located near corners of the block on opposite sides of the slots. Another aperture, for receiving a temperature sensor or probe, is preferably located in close proximity to the slots.

The described arrangement produces a substantially isothermal region surrounding the slots as well as the temperature sensor aperture. As a result, absolute temperature measurement accuracy is significantly improved. In addition, because a substantially uniform temperature is maintained across all of the slots, improvement is also attained in terms of repeatability of test results.

The heater assembly is simple and inexpensive to manufacture, rugged and reliable in operation, and may be readily disassembled for the purpose of repairing or replacing components.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
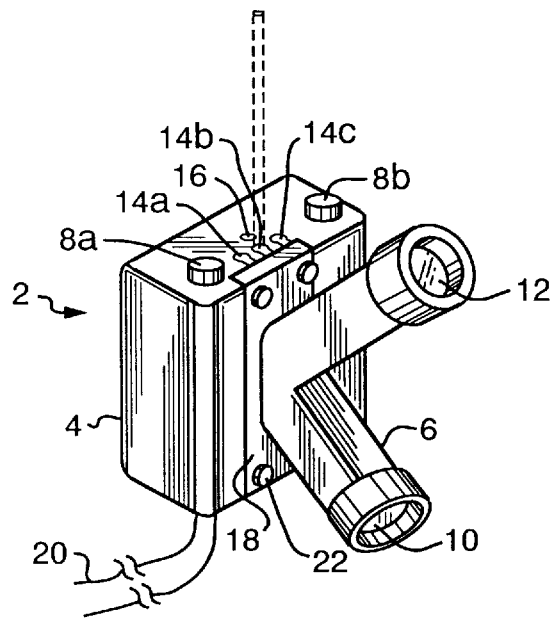
FIG. 1 is a perspective view of a block-type heater assembly constructed in accordance with a preferred embodiment of the present invention.

FIG. 1 shows a block-type beater assembly 2 which may be used, for example, in connection with a melting point/ boiling point determination apparatus, some examples of which are disclosed in the co-pending application incorporated by reference above.

The major components of heater assembly 2 are a block 4 having a substantially rectangular cross-section, an optical assembly 6 which is attached by a flange 18 and fasteners 22 to a recessed area formed in one of the broad faces of block 4, and two cylindrical, electric heating elements 8a and 8b. A slot or passage 16 for receiving a temperature sensor or probe (not shown) is located in close proximity to three passages or slots 14a–14c. A pair of leads 20 connect each of heating elements 8a and 8b to a control unit (not shown), Optical assembly 6 includes a light diffuser 10 for directing a light source (not shown) toward the lower portions slots 14a–14c which are arranged in a substantially vertical orientation and extend downward from the top surface of block 4 to approximately the middle of the block Optical assembly 6 also includes a magnifying lens 12 for allowing a user to visually observe the bottom portions of sample-containing glss capillary tubes which may be present in slot 14a–14c (one such tube being shown in phantom), Slots 14a–14c are preferably shaped and dimensioned to closely fit with the capillary tubes or similar containers for holding samples which are to be tested, one such tube shown in phantom.

It should be understood that other devices may be substituted for optical assembly 6 to provide desired observation capability for a user or a machine-based system. As described below, block 4 provides a surface to which any of a number of devices for observing the samples may be conveniently mounted.

Figure 2:
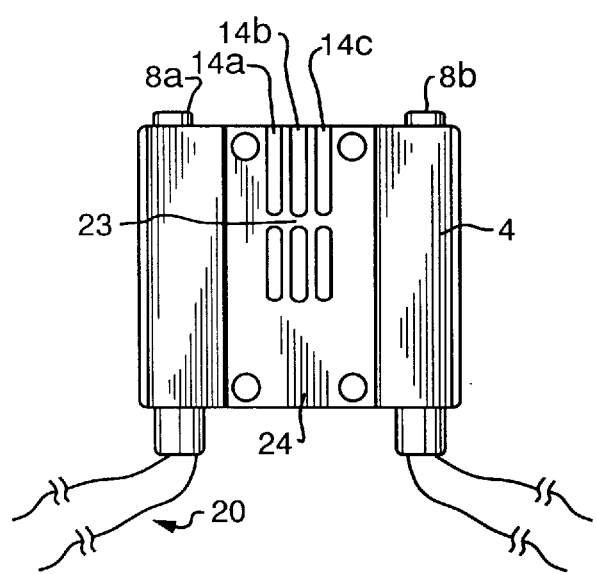
FIG. 2 is a front elevation view of the heater block of FIG. 1.
Figure 4:
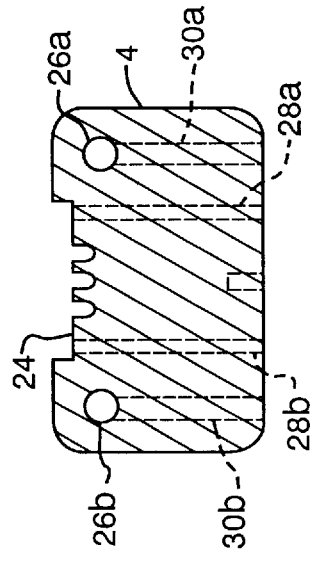
FIG. 4 is a section taken along line 4—4 of FIG. 3.
Figure 3:
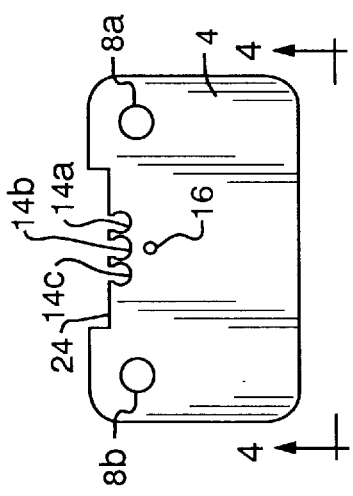
FIG. 3 is a top plan view of the heater block of FIG. 1.

As may be seen best in FIGS. 2, 3 and 4, in which optical assembly 6 is omitted for purposes of improved clarity, a recessed area 24 extends along the length of block 4. Recessed area 24 is shaped and dimensioned to provide a close-fitting mounting surface for flange 18, and to prevent flange 18 from making direct contact with any of the capillary tubes placed in slots 14a–14c. This arrangement is preferable to prevent irregularities or imperfections on the surface of flange 18 from affecting the fit of the capillary tubes within slots 14a–14c and from, creating undesirable temperature variations among those slots. A web 23 extends laterally across slots 14a–14c and acts as a barrier to prevent heated air trapped within optical assembly 6 from escaping and undesirably cooling the capillary tubes and samples contained therein.

Two through holes 26a and 26b are provided to accommodate heating elements 8a and 8b, respectively, Four though holes 28a and 28b are provided to accommodate fasteners 22. Holes 30a and 30b accommodate set screws (not shown) for securing heating elements 8a and 8b.

Block 4 is preferably constructed of aluminum or another material which is a good thermal conductor and may be manufactured using conventional machining techniques. Such machining is somewhat costly due to the number of small diameter, relatively deep bores required. Alternatively, the block, with slight modifications described below in connection with FIG. 5, may be manufactured by extrusion techniques at a lower cost. Heating elements 8a and 8b are commercially available components and optical assembly 6 may be constructed from commercially available components.

Figure 5:
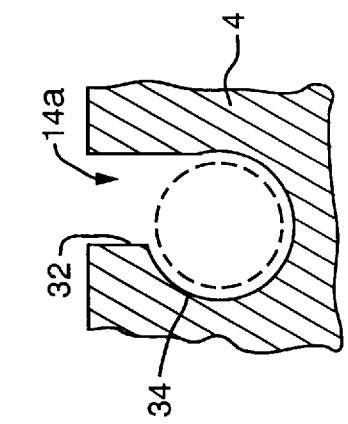
FIG. 5 is an enlarged section of one of the capillary tube passages in the block of FIG. 1.

FIG. 5 is an enlarged section of slot 14a whose shape is representative of the other capillary tube slots. Preferably, a bore 34 is slightly laterally displaced with respect to a viewing passage 32. This arrangement provides at least two significant advantages. First, it permits a user to clearly observe one side of the capillary tube (shown in phantom) and the sample contained therein during the heating process. This is important since the samples melting usually begins right at the capillary's inner wall. Second, it increases the amount of the surface area of the capillary tube which is in proximity to the material of block 4, which tends to enhance the transfer of thermal energy to the tube.

Referring again to FIGS. 1 and 2, computer simulations and test results have shown that the use of at least two heating elements 8a and 8b, along with placement of capillary tube slots 14a–14c in an essentially straight line between the heating elements, results in the generation of a substantially isothermal region which envelopes slots 14a–14c as well as temperature probe slot 16. In effect, the positions of the heating elements with respect to each other and the slots establishes a relationship in which thermal losses (cooling) caused by the necessary presence of optical assembly 6 are prevented from creating a temperature gradient among the slots. Because heating elements 8a and 8b preferably extend the full length of block 4, the isothermal region extends three-dimensionally through a substantial portion of the thickness of the block. Further, by shaping block 4 such that a substantial volume of thermally conductive material is present "behind"(i.e., opposite from optical assembly 6)the slots, the thermal stability of the assembly is enhanced.

Figure 6:
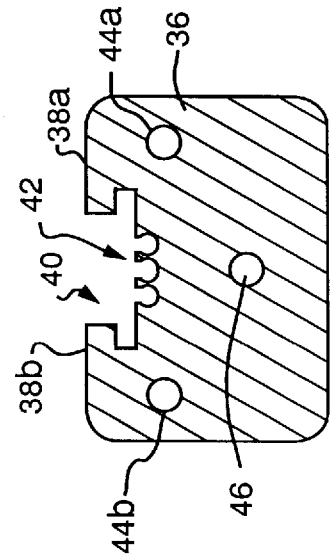
FIG. 6 is a section of an alternative embodiment of the hater block of FIG. 1 which may be manufactured using extrusion techniques.

FIG. 6 shows in cross-section a block 36 which is similar to block 4 of FIGS. 1–5, but modified to take advantage of extrusion manufacturing techniques. Integral shoulders 38a and 38b define a T-shaped channel or recessed arca for mounting optical assembly 6. Three capillary tube slots 42 are provided as before. Two through holes 44a and 44b are provided to accommodate heating elements (not shown). A temperature sensor passage 46 is also provided.

The foregoing description has been limited to specific embodiments of his invention. It will be apparent, however, that variations and modifications may be made to the invention, with the attainment of some or all of the advantages of the invention. Therefore, it is the object of the appended claims to cover all such variations and modifications as come within the true spirit and scope of the invention.

What is claimed as new and desired to be secured by Letters Patent of the United States is:

1. A block-type heater assembly for enabling a user to visually observe one or more samples while said samples are being heated, said assembly comprising:

a volume of thermally conductive material, one or more first passages each for receiving a container for holding one of said samples, at least one second passage for receiving a temperature sensor, and a plurality of heating elements arranged to generate a substantially isothermal region which includes all of said first and second passages; and optical means coupled to said volume and arranged to permit a user to visually observe said samples wherein said optical means is positioned with respect to said first and second passages and said heating elements so as to substantially prevent a temperature gradient among said first and second passages.

2. The block-type heater assembly of claim 1 wherein a depth of said second passage is substantially matched to a depth of said first passages, whereby said temperature sensor is disposed proximal to said samples and the center of said volume along an axis parallel to said first passages.

3. The block-type heater assembly of claim 1 wherein said volume of thermally conductive material has a substantially rectangular cross-section, and wherein said plurality of heating elements comprises two heating elements arranged such that said first and second passages are located between said elements within said substantially isothermal region.

4. The block-type heater assembly of claim 3 wherein said two heating elements are generally cylindrical in shape and each has a longitudinal axis oriented substantially parallel to said first and second passages, and wherein each of said two heating elements is near an edge of said substantially rectangular cross section, thereby generating a substantially isothermal three dimensional region around said first and second passages.

5. The block-type heater assembly of claim 1 wherein said volume of thermally conductive material is shaped and dimensioned to permit manufacture by an extrusion process.

6. The block-type heater assembly of claim 1 wherein the one or more first passages each includes a viewing portion open to said optical means, each of said first passages being slightly laterally displaced with respect to its associated viewing portion.

7. The block-type heater assembly of claim 1 wherein each container for holding one of said samples has an outside perimeter, and wherein each of said one or more first passages includes webbing for receiving one of said containers such that said webbing closely engages said outside perimeter, thereby preventing escape of air from the first passage receiving the container.

8. The block-type heater assembly of claim 1 wherein said volume of thermally conductive material is solid and has a thickness which is substantially greater than a distance between any two of said first passages.

9. The block-type heater assembly of claim 1 wherein said first passages are sufficiently recessed within said volume such that any imperfections of said optical means do not interfere with the fit of the sample containers in the first passages.

10. The block-type heater assembly of claim 3 wherein the optical means is substantially centered between the two heating elements.

11. The block-type heater assembly of claim 3 wherein said first passages are substantially centered between the two heating elements.

12. The block-type heater assembly of claim 3 wherein said second passage is substantially centered between the two heating elements.

13. The block-type heater assembly of claim 1 wherein said second passage is disposed in proximity to said first passages, said proximity not exceeding approximately one times a diameter of one of said first passages.

14. The block-type heater assembly of claim 1 wherein a sidewall thickness of said first passages is not less than one times a diameter of one of said first passages.

15. The block-type heater assembly of claim 1 wherein said volume of thermally conductive material is sufficiently long in comparison with a length of said first passages to substantially prevent uneven temperatures at the surface of said volume from affecting said samples.

* * * * *